United States Patent [19]
Fouts

[11] Patent Number: 5,692,505
[45] Date of Patent: Dec. 2, 1997

[54] DATA PROCESSING SYSTEMS AND METHODS FOR PULSE OXIMETERS

[76] Inventor: James Michael Fouts, 514 176th La., Northeast, Bellevue, Wash. 98008

[21] Appl. No.: 641,993

[22] Filed: Apr. 25, 1996

[51] Int. Cl.$^6$ ............................................. A61B 5/00
[52] U.S. Cl. ................................. 128/633; 356/41
[58] Field of Search ........................ 128/633, 664, 128/665, 666, 667; 356/39, 40, 41

[56] References Cited

U.S. PATENT DOCUMENTS

| | | | |
|---|---|---|---|
| 5,482,036 | 1/1996 | Diab et al. | 128/633 |
| 5,490,505 | 2/1996 | Diab et al. | 128/633 |

*Primary Examiner*—Jennifer Bahr
*Assistant Examiner*—Eric F. Winakur
*Attorney, Agent, or Firm*—Seed and Berry LLP

[57] ABSTRACT

An improved circuit for processing the received signals of a pulse oximeter includes at least first and second light-emitting diodes for transmitting light of first and second frequencies toward the finger of a user. The first diode is responsive to a first control signal for transmitting light of the first frequency. The second diode is responsive to a second control signal for transmitting light of the second frequency. Also, the first diode is responsive to a modulated control signal for transmitting a modulated light signal also of the first frequency. A photodetector is constructed to receive a first composite signal, representing the amount of light transmitted by the first diode in response to the first control signal, and a second composite signal, representing the amount of light transmitted by the second diode in response to the second control signal, wherein the first and second composite signals each include a desired signal portion and an undesired signal portion. The photodetector also receives a noise signal representing the amount of light transmitted through the finger by the first diode in response to the modulated control signal. The first and second composite signals are adaptively combined with the noise signal to provide the desired signal portion of the first and second signals, wherein the ratio of the desired signal portions represent the red to infrared ratio of the pulse oximeter. The red to infrared ratio of the pulse oximeter is combined with the second composite signal to provide the modulated control signal.

13 Claims, 1 Drawing Sheet

DATA PROCESSING SYSTEMS AND METHODS FOR PULSE OXIMETERS

TECHNICAL FIELD

The present invention is directed toward pulse oximeters and, more particularly, toward an improved data processing method and apparatus for use in combination with pulse oximeters.

BACKGROUND OF THE INVENTION

Pulse oximeters for determining the oxygen saturation levels of a blood sample contained in a medium are well known. Generally, pulse oximeters rely upon transmitting light at red and near infrared frequencies toward the blood sample. In most useful and practical applications, the medium that contains the blood sample will be human or animal tissue. As examples, prior art pulse oximeters have transmitted light at red and infrared frequencies through a finger of the subject or an earlobe of the subject.

A detector is used to determine the magnitude of light that is transmitted through the medium. The detected magnitude of light is used to generate patient signals that are indicative of the oxygen saturation levels of the blood sample. Pulse oximeters generally rely upon the principal that the absorption of light in blood is dependent upon the oxygen saturation levels of the blood sample and the frequency of the transmitted light, i.e., red or near infrared. By calculating a ratio of the magnitude of light transmitted through the medium at the red and infrared frequencies, and further calculating oxygen saturation using calibration coefficients embodied in look-up tables, or the like, pulse oximeters can determine the oxygen saturation levels of blood samples.

One major drawback, however, to the use of pulse oximeters is that the detected magnitude of light, and hence the patient signals, are affected by noise introduced by the medium in which the blood sample is contained. Typically, the signal-to-noise ratio of the patient signals is very low, i.e., noise is a large percentage of the patient signals. One major source of noise results from changes in the optical pathway due to motion of the patient. This noise source is typically referred to as "motion artifact." Prior art pulse oximeters have been unable to eliminate noise created by motion artifact.

Most prior art methods attempt to reduce the effect of motion artifact instead of removing the noise that results from motion artifact. One prior art method for reducing the effect of motion artifact relies upon selecting a portion of the patient's body that can remain relatively still during the measurement interval. These methods have proven unsuccessful since motion that results in noise originates from involuntary, as well as voluntary, motion of the patient, e.g., motion that results from blood pulsations in the medium being measured. Even this minute motion has been known to introduce substantial noise and resulting error in a pulse oximetry calculation.

Other prior art techniques for removing noise resulting from motion artifact rely upon extensive calculations being performed on data obtained from the patient signals. One such method attempts to evaluate a large amount of data and determine whether the data is consistent with predetermined shape characteristics that are indicative of patient pulsating arterial blood. At times when the data is consistent with the predetermined shape characteristics, the systems assume that motion artifact is at a minimum and that the data, therefore, accurately reflects the oxygen saturation levels of the blood sample. At times when the data is not consistent with the predetermined shape characteristics, the system assumes that motion artifact has affected the data and that the data is not accurate. These systems, however, are not desirable since even when the patient signal approximates the predetermined shape characteristic, noise from motion artifact will be present rendering the measurement at least partially inaccurate. Also, some actual noise-free patient signals have a shape resembling noise, rather than an arterial pulse. Furthermore, on occasion, noise that results from motion artifact can approximate the predetermined shape characteristic, in which case, the patient signal is not likely to be accurate at all.

Still other methods for eliminating noise due to motion artifact in pulse oximeters rely upon averaging data received from the patient signal in combination with elaborate weighting schemes to determine the saturation level. However, like the pulse oximeters described above, the data that is used for determining the oxygen saturation level in these pulse oximeters include noise that results from motion artifact. Therefore, the corrected oxygen saturation levels will still be somewhat inaccurate. Furthermore, by their nature, the device cannot completely compensate for the effects of motion artifact, but can only reduce its effect through averaging and weighting.

Still another technique for processing data received from patient signals to mathematically correct for errors caused by motion artifact relies upon calculating one saturation level for each received patient cardiac pulse. The saturation level is calculated using a maximum signal and a minimum signal technique. This method makes the assumption that the signal-to-noise ratio will be maximized to get a best average saturation. Like the methods discussed above, this method does not attempt to eliminate noise that results from motion artifact but only to minimize the effects of that noise.

Moreover, recognizing that presently available methods for processing data received from patient signals to correct for motion artifact do not eliminate the effect of noise, some practitioners have resorted to using one or more of the above-described methods with an additional safeguard. These practitioners provide a clinician with a representative plethysmographic waveform for analysis. The clinician determines if the calculated saturation value is accurate. Obviously, the use of this safeguard detracts from the value of providing an automated system for determining oxygen saturation.

Accordingly, it is desirable to provide method and apparatus for determining an accurate oxygen saturation level of a blood sample in the presence of motion artifact. Also, it is desirable to provide method and apparatus for eliminating any noise that may be present in the patient's signals as a result of motion artifact.

SUMMARY OF THE INVENTION

The present invention is an improved circuit for use with a pulse oximeter to determine a signal ratio, wherein the signal ratio is combined with look-up tables to determine the oxygen saturation levels of a blood sample. The circuit includes light-emitting elements that are responsive to first and second control signals for emitting light signals of respective first and second frequencies. The light-emitting elements are further responsive to a modulation signal for emitting a modulated light signal of the first frequency. The circuit includes a photodetector assembly for providing first and second composite signals respectively indicative of the amount of light received from the first and second light signals, wherein the first and second composite signals each include a desired signal portion and a noise signal portion. The photodetector assembly also provides a noise signal that is indicative of the amount of light received from the modulated light signal. A data processor is provided for combining the first composite signal with the noise signal to provide a first desired signal. Similarly, the data processor combines the second composite signal with the noise signal to provide a second desired signal. The data processor determines the signal ratio as a ratio of the magnitudes of the first and second desired signals. Moreover, the data processor combines the signal ratio and the second composite signal to provide the modulation signal. The data processor transmits the first and second control signals, along with the modulation signal, to the light-emitting elements.

In a particular embodiment of the invention described above, the data processor is constructed to perform adaptive noise canceling for removing the noise signal portion from the first and second composite signals to provide the respective first and second desired signals.

DETAILED DESCRIPTION OF THE INVENTION

Figure 1:
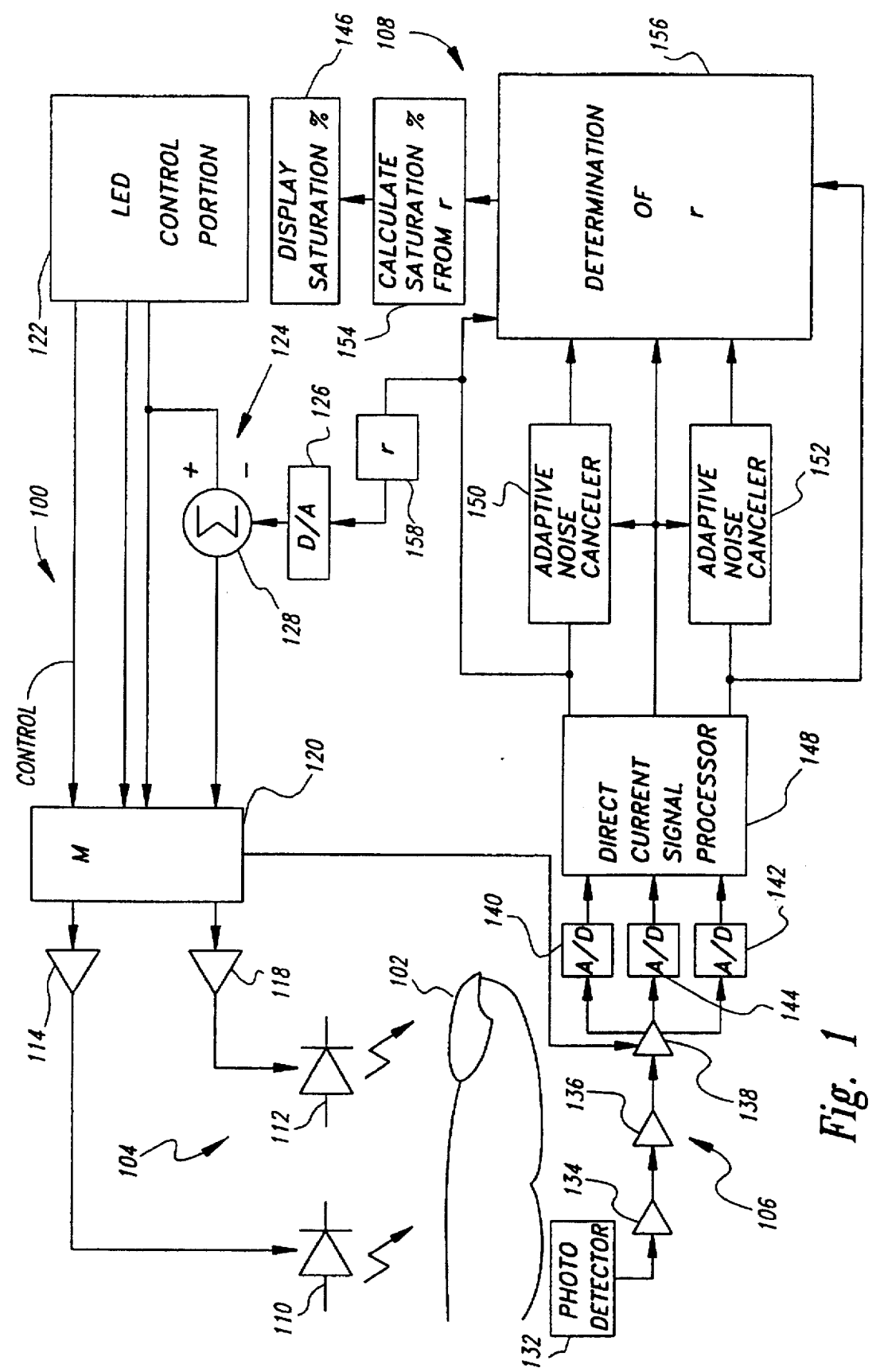
FIG. 1 is an illustration of the improved circuit for processing signals in a pulse oximeter.

A pulse oximeter 100, constructed in accordance with the present invention, is illustrated in FIG. 1. The pulse oximeter 100 is designed to determine the oxygen saturation level of a blood sample contained in a medium. In the illustration of FIG. 1, the blood sample is contained in a finger 102 of a user. The pulse oximeter 100, however, can be readily constructed to determine the oxygen saturation of any patient tissue containing a blood sample. Furthermore, the pulse oximeter 100 can be constructed and used to determine the oxygen saturation levels of any blood sample contained in any medium.

The pulse oximeter 100 generally includes a light-emitting assembly 104 that is responsive to first and second control signals for emitting light signals of respective first and second frequencies. As is known in the art, pulse oximeters generally are constructed to emit light in the red and near infrared frequencies. Those skilled in the art typically refer to the signal transmitted at these first and second frequencies as the red signal and the infrared signal. However, the light-emitting assembly 104 may be constructed to emit first and second light signals of varying frequencies.

The light-emitting assembly 104 is further responsive to a modulation signal for emitting a modulated light signal of the first frequency. As illustrated in FIG. 1, the light emitted by the light-emitting assembly 104 is transmitted toward the finger 102 of the user.

A light-detecting assembly 106 is positioned proximate the finger 102 of a user for receiving light transmitted through the finger by the light-emitting assembly 104. The light-detecting assembly 106 is constructed to provide first and second composite signals that are respectively indicative of the amount of light received from the first and second light signals. The first and second composite signals each include a desired signal portion and a noise signal portion. Generally, the noise signal portion is a result of motion artifact. However, those skilled in the art will recognize that the noise signal portion can be a combination of noise resulting from motion artifact with noise resulting from other common noise sources.

The light-detecting assembly 106 is further constructed to provide a noise signal that is indicative of the mount of light received from the modulated light signal. As will be described in greater detail below, the modulation signal provided to the light-emitting assembly 104 is selected so that after being transmitted through the finger 102 of the user, the detected signal will include a component indicative of the noise signal portion of the first composite signal and a component indicative of the noise signal portion of the second composite signal. As is further described below, the noise signal is adaptively combined with the first and second composite signals to provide first and second desired signals, respectively, representing the first and second desired signal portions of the first and second composite signals.

The pulse oximeter 100 further includes a data processing assembly 108 coupled to the light-detecting assembly 106 for receiving the first and second composite signals and the noise signal. The data processing assembly 108 is constructed to combine the first composite signal with the noise signal to provide a first desired signal. The data processing assembly 108 is also constructed to combine the second composite signal with the noise signal to provide a second desired signal. The data processing assembly 108 determines a signal ratio, wherein the signal ratio is a ratio of the magnitudes of the first and second desired signals. When the first and second desired signals represent a red signal and an infrared signal, as discussed above, the signal ratio is referred to as the ratio of red to infrared and is designated using a small r. As will be discussed further below, this ratio is combined with data stored in a lookup table to determine the oxygen saturation levels of blood contained in the blood sample.

The data processing assembly 108 combines the signal ratio and the second composite signal from the light-detecting assembly 106 to provide the modulation signal. It will be apparent to those skilled in the art that since the second composite signal is a combination of a second desired signal portion and a second noise portion, and since the signal ratio is a ratio of the magnitudes of the first and second desired signal portion, proper combination of the signal ratio with the second composite signal will provide a modulation signal that includes a term representing the first desired signal portion and a term representing the second noise signal portion. Advantageously, when the modulation signal is used to modulate the light of the first frequency from the light-emitting assembly 104, the term representing the first desired signal portion will be canceled during transmission through the finger 102, thereby leaving the noise signal which includes a term representing the first noise signal portion and a term representing the second noise signal portion, as discussed above.

The light emitting assembly 104, light-detecting assembly 106, and data processing assembly 108, can each be constructed from commercially available components. Similarly, prior art pulse oximeters can be reconstructed to operate in accordance with the invention as illustrated and described by reference to the pulse oximeter 100.

More particularly, the light-emitting assembly 104 may include first and second light-emitting diodes 110 and 112 constructed to emit light of respective first and second predetermined frequencies. As discussed above, the frequencies typically selected for pulse oximetry are frequencies in the red frequency spectrum, approximately 660 nanometers, and frequencies near the infrared frequency spectrum, approximately 940 nanometers. The first and second light-emitting diodes 110 and 112 are each positioned proximate the finger 102 of the user so that the light can be transmitted through the finger.

The first and second light-emitting diodes 110 and 112 are driven by first and second drivers 114 and 118, respectively. The first and second drivers 114 and 118 are each provided for supplying power to their input signals to adequately drive the first and second light-emitting diodes 110 and 112. A time division multiplexer 120 is controlled by the data processing assembly 108 to provide the input signals to the first and second drivers 114 and 118, as described more fully below. Advantageously, the first light-emitting diode 110 is constructed to vary the intensity of light in accordance with variation in the amplitude of the signal received from the multiplexer 120. Since the modulation signal provided by the data processing assembly 108 is a signal that varies in amplitude, the light emitted by the first light-emitting diode 110 in response to the modulation signal will vary in intensity.

The time division multiplexer 120 receives first and second control signals from an LED control portion 122 of the data processing assembly 108. The first and second control signals provided to the time division multiplexer 120 by the LED control portion 122 comprise substantially direct current signals so that the light emitted by the first and second light-emitting diodes 110 and 112 in response to these signals will be a substantially constant amplitude and frequency light signal. The LED control portion 122 also provides the first control signal to a signal combining assembly 124, which combines the first control signal with the modulation signal to provide a modulated control signal. It is the modulated control signal that is provided to the first light-emitting diode 110 through the time division multiplexer 120 and the first driver 114.

The signal combining assembly 124 includes a digital-to-analog converter 126 that receives the modulation signal from the data processing assembly 108 and converts the modulation signal to an analog signal. The modulation signal is combined with the first control signal in a signal combiner 128. The signal combiner 128 adds the first control signal to the analog modulation signal to provide the modulated control signal. Essentially, the signal combiner 128 provides a DC offset to the modulation signal.

Although the signal combiner assembly 124 has been described herein by reference to a signal combiner 128 that is essentially a signal adder for adding the substantially direct current second control signal to the modulation signal, those skilled in the art will recognize that other constructions for the signal combining assembly and/or the second control signal may be readily provided without departing from the present invention. The important function of the signal combiner is to permit a varying amplitude signal to be provided to the first light-emitting diode 110 so that when transmitted through the finger 102, the signal portion of the varying amplitude signal will be canceled and the output will include a noise signal having two components, wherein a first component represents the noise obtained as a result of the first frequency transmission, i.e., as a result of transmitting the substantially constant amplitude and frequency light from the first light-emitting diode 110, and wherein a second component represents the noise obtained from the second frequency transmission, i.e., as a result of transmitting the substantially constant amplitude and frequency light from the second light-emitting diode 112.

The time division multiplexer 120 is constructed to provide the first and second control signals and the modulated control signal sequentially, so that the constant amplitude light of the first frequency, the constant amplitude light of the second frequency, and the modulated amplitude light of the first frequency are sequentially provided to the finger 102. Furthermore, the time division multiplexer 120 provides a control signal to the light-detecting assembly 106, indicating which signal is being provided. In this manner, the light-detecting assembly 106 can determine the source of the received light.

The light-detecting assembly 106 includes a photodetector 132 that is constructed to detect the light emitted by the first and second light-emitting diodes 110 and 112. The photodetector output is coupled to an amplifier 134 and a low pass filter 136 for respectively amplifying and filtering the received signal. A synchronous demodulator 138 receives the output from the low pass filter 136 and the control signal from the time division multiplexer 120 and demodulates the received signal, with respect to time, to provide three light detector output signals. The first light detector output signal is associated with light received from the first light-emitting diode 110 in response to the first control signal. Similarly, the second light detector output signal is associated with light received from the second light-emitting diode 112 in response to the second control signal. The third light detector output signal is associated with light received from the first light-emitting diode 110 in response to the modulated control signal.

The amplifier 134, low pass filter 136, and synchronous demodulator 138 act as conditioning circuits to remove undesired signal portions of the frequency spectrum of the output from the photodetector 132. The undesired signal portions typically represent sidebands and harmonics of the desired signal that may be readily filtered using conventional technology, e.g., low pass filtering. Furthermore, the signal conditioning can be used to reject noise resulting from ambient light sources. In addition, the signal conditioning may be used to amplify or otherwise condition the output from the photodetector 132 for use by the data processing assembly 108. Other conditioning that may be provided to the output from the photodetector 132 will readily become apparent to those skilled in the art.

The outputs from the synchronous demodulator 138 are provided to first, second, and third analog-to-digital converters 140, 142, and 144. The first, second, and third analog-to-digital converters are constructed to convert the first, second, and third light detector output signals to respective first, second, and third digital signals wherein the first digital signal is associated with light received from the first light-emitting diode in response to the first control signal, the second digital signal is associated with light received from the second light-emitting diode 112 in response to the second control signal, and the third digital signal is associated with light received from the first light-emitting diode 110 in response to the modulated control signal. The analog-to-digital converters 140, 142, and 144 provide the output of the light detecting assembly 106.

As discussed above, the output from the light-detecting assembly 106 is provided to the data processing assembly 108. The data processing assembly 108 is responsive to the first, second, and third light detector output signals to calculate the oxygen saturation level of the blood sample in the finger 102, to provide the modulation signal to the light-emitting assembly 104, and to provide the first, second, and third control signals to the light-emitting assembly 104. The data processing assembly 108 includes a display 146 for displaying the determined oxygen saturation levels. Further, the data processing assembly 108 may include a keyboard (not shown) or other apparatus for permitting a user to provide input to the pulse oximeter 100.

Those skilled in the art will appreciate that many conventional elements may be used to construct the data processing assembly 108. As examples, a standard personal computer can be coupled with appropriate interfaces and software programming to perform the functions of the data processing assembly 108. Similarly, a microprocessor circuit may be provided with the appropriate interfaces and software programming to perform these functions. Also, programmable integrated circuits such as gate arrays in combination with conventional logical elements may be used to construct circuitry for performing the functions of the data processing assembly 108. Accordingly, although the data processing assembly 108 is described hereinbelow by reference to elements performing specified functions, those skilled in the art will recognize that in some, if not most, applications these functions will be implemented in software using a data computing-type device.

The data processing assembly 108 includes a direct current signal processor 148 for removing the direct current component of the first, second, and third digital signals. The direct current signal processor 148 is also constructed to normalize one of the first or second digital signals with the direct current component of the first and second digital signals, e.g., is constructed to normalize either the red or the infrared signal with the ratio of the direct current components of the red-to-infrared signals, as is known in the art. The direct current signal processor 148 provides the normalized first digital signal with the direct current component removed as the first composite signal; the second digital signal with the direct current component removed as the second composite signal; and the third digital signal with the direct current component removed as the noise signal. Those skilled in the art will appreciate that although the invention is described herein as normalizing the first digital signal, either the first or second digital signal may be normalized.

The output from the direct current signal processor 148 is provided to first and second adaptive noise cancelers 150 and 152. The first adaptive noise canceler 150 is responsive to the first composite signal and the noise signal for removing the noise signal portion from the first composite signal to provide a first desired signal. The second adaptive noise canceler 152 is responsive to the second composite signal and the noise signal for removing the noise signal portion from the second composite signal to provide a second desired signal. In one presently preferred embodiment of the invention, the first and second adaptive noise cancelers are constructed in accordance with adaptive signal processing techniques similar to those discussed in "Adaptive Signal Processing," by Widrow et al. (Prentice-Hall, Inc., 1985). However, those skilled in the art will appreciate that any technique for combining a noise signal with a signal having a desired signal portion and noise signal portion, wherein the technique is used to cancel the noise signal portion and provide as its output the desired signal portion, may be used for the adaptive noise cancelers 150 and 152.

A memory assembly 154 is constructed for storing a lookup table for correlating values of a signal ratio to the oxygen saturation level of a user's blood. Such lookup tables are standard and well known in the industry.

A digital processor 156 is constructed to determine the value of r. As discussed above, r represents the ratio of the first and second desired signals, or the red-to-infrared ratio. The signal processor 156 responds to the memory assembly 154 for determining the oxygen saturation level of the blood sample of the user. The determined oxygen saturation level is provided to the display 146 for displaying the information to the user or an operator.

The data processing assembly 108 includes a multiplying portion 158 for combining the signal ratio r and the second composite signal to provide the modulation signal. In the presently preferred embodiment of the invention, the multiplication portion 158 multiplies the second composite signal by the signal ratio to provide the modulation signal. However, other methods for combining the signal ratio and the first composite signal (i.e., combining the red or infrared signal with the ratio of red to infrared) may be selected in accordance with the present invention. Those skilled in the art will note, however, that if the modulation signal is to be transmitted at the second frequency, then the multiplication portion 158 must combine the signal ratio with the composite signal received at the first frequency and, vice versa. Furthermore, those skilled in the art will recognize that if the modulation signal is to be transmitted at the second frequency, then the multiplication portion 158 must combine the inverse of the signal ratio with the composite signal received at the first frequency and that this combination will be a multiplication of the inverse of the signal ratio with the first composite signal.

In operation, the light-detecting assembly 106 provides the noise reference signal in response to transmission of light from the first diode 110 and the modulated control signal. Generation of the noise reference signal is explained by reference to the following mathematical model. Therein, the signals received from the first and second diodes 110 and 112 in response to the first and second control signals can be expressed as:

$$S_{\lambda a}=d_{\lambda a}+u_{\lambda a} \quad (1)$$

$$S_{\lambda b}=d_{\lambda b}+u_{\lambda b} \quad (2)$$

wherein S represents a composite signal having a desired signal portion and an undesired signal portion, d represents the desired signal portion of the composite signal, u represents the undesired signal portion of the composite signal, and the subscripts $\lambda a$ and $\lambda b$ refer to the light sourced from the first and second diodes 110 and 112 in response to the substantially constant amplitude first and second control signals, respectively.

As is known in the art, the signal ratio r is the ratio of the desired signal portions and is expressed as follows:

$$r=d_{\lambda a}/d_{\lambda b}. \quad (3)$$

Since the modulation signal is the product of a digitized continuous signal which is then used to generate the Noise Reference, an error will exist in the Noise Reference that is the difference in value of the waveform sample of $S_{\lambda b}$ at the present time and the previous sample $S_{\lambda b}'$. The sample rate will be chosen such that this error will be insignificant. That is to say:

$$S_{\lambda b}=S_{\lambda b}' \quad (4)$$

$$d_{\lambda b}=d_{\lambda b}' \quad (5)$$

$$u_{\lambda b}=u_{\lambda b}' \quad (6)$$

The modulation signal is equal to the second composite signal multiplied by the signal ratio, i.e., $r*S_{\lambda b}$, so that the signal received by the diode 110 in response to the modulated control signal, i.e., the noise reference signal, can be expressed as follows:

$$\text{Noise Reference}=S_{\lambda a}-r*S_{\lambda b}'. \quad (7)$$

Using the relationships of equations (1) and (2), the noise reference signal can be expanded as follows:

$$\text{Noise Reference}=(d_{\lambda a}+u_{\lambda a})-r*(d_{\lambda b}'+u_{\lambda b}'). \quad (8)$$

Rewriting equation (3) and using equation (5):

$$d_{\lambda b} = d_{\lambda a}/r \quad (9)$$

then substituting into equation (8), the noise reference signal can be expressed as follows:

$$\text{Noise Reference} = d_{\lambda a} + u_{\lambda a} - r*d_{\lambda a}/r - r*u_{\lambda b} \quad (10)$$

canceling terms and using substitution (6) gives:

$$\text{Noise Reference} = u_{\lambda a} - r*u_{\lambda b} \cong u_{\lambda a} - r*u_{\lambda b} \quad (11)$$

This noise reference signal is provided by the direct current signal processor 148 to the adaptive noise cancelers 150 and 152 and to the digital processor 156.

From the foregoing it will be appreciated that, although specific embodiments of the invention have been described for purposes of illustration, various modifications may be made without deviating from the spirit and scope of the invention. Accordingly, the invention is not limited except as by the appended claims.

I claim:

1. An improved circuit for use with a pulse oximeter to determine a signal ratio, wherein the signal ratio is used to determine the oxygen saturation levels of a blood sample, said circuit comprising:

light-emitting means responsive to first and second control signals for emitting light signals of respective first and second frequencies, said light-emitting means being further responsive to a modulation signal for emitting a modulated light signal of the first frequency;

light detector means for providing first and second composite signals respectively indicative of the amount of light received from the first and second light signals, wherein the first and second composite signals each include a desired signal portion and a noise signal portion, said light detector means also for providing a noise signal indicative of the amount of light received from the modulated light signal; and data processing means for combining the first composite signal with the noise signal to provide a first desired signal and for combining the second composite signal with the noise signal to provide a second desired signal, said data processing means also determining the signal ratio wherein the signal ratio is a ratio of the magnitudes of the first and second desired signals, said data processing means further combining the signal ratio and the second composite signal to provide the modulation signal, said data processing means also providing the first and second control signals.

2. The improved circuit as recited in claim 1 wherein said data processing means further comprises adaptive noise canceler means responsive to the first composite signal and the noise signal for removing the noise signal portion from the first composite signal to provide the first desired signal and responsive to the second composite signal and the noise signal for removing the noise signal portion from the second composite signal to provide the second desired signal.

3. The improved circuit as recited in claim 1 wherein said light-emitting means further comprises:

a first light-emitting diode responsive to the first control signal for emitting light of the first predetermined frequency; and a second light-emitting diode responsive to the second control signal for emitting light of the second predetermined frequency.

4. An improved pulse oximeter for measuring the oxygen content of a blood sample of a user, comprising:

a first light-emitting diode responsive to a first control signal for emitting light of a first predetermined frequency, said first light-emitting diode being constructed to be positioned proximate the user to emit light of the first predetermined frequency toward the user;

a second light-emitting diode responsive to a second control signal and a modulated control signal for emitting light of a second predetermined frequency, said second light-emitting diode being constructed to be positioned proximate the user to emit light of the second predetermined frequency toward the user;

photodetector means for providing first and second composite signals respectively indicative of the amount of light received from said first light-emitting diode in response to the first control signal and from said second light-emitting diode in response to the second control signal, wherein the first and second composite signals each include a desired signal portion and a noise signal portion, said photodetector means also for providing a noise signal indicative of the amount of light received from said first light-emitting diode in response to the modulated control signal;

adaptive noise canceler means responsive to the first composite signal and the noise signal for removing the noise signal portion from the first composite signal to provide a first desired signal and responsive to the second composite signal and the noise signal for removing the noise signal portion from the second composite signal to provide a second desired signal;

data processing means for determining a signal ratio and for determining the percentage of oxygen in the user's blood wherein the signal ratio is a ratio of the magnitudes of the first and second desired signals, said data processing means being further constructed to combine the signal ratio and the second composite signal to provide a modulation signal, said data processing means also being constructed to provide the first and second control signals and a third control signal;

signal combining means for combining the third control signal and the modulation signal to provide the modulated control signal; and display means responsive to said data processing means for displaying the percentage of oxygen in the user's blood.

5. The improved pulse oximeter as recited in claim 4 wherein said photodetector means further comprises signal processing means for removing undesired portions of the frequency spectrum of the first and second composite signals and the noise signal.

6. The improved pulse oximeter as recited in claim 4 wherein said photodetector means further comprises analog to digital conversion means for converting the first and second composite signals and the noise signal into respective digital signals.

7. The improved pulse oximeter as recited in claim 4 wherein said photodetector means further comprises direct current signal processing means for removing the direct current component of the second composite signal and the noise signal, said direct current signal processing means also for removing the direct current component of the first composite signal and for normalizing the first composite signal with the direct current components of the first and second composite signals.

8. The improved pulse oximeter as recited in claim 4 wherein said data processing means further comprises memory means for storing a lookup table for correlating values of the signal ratio to the percentage of oxygen in a user's blood.

9. The improved pulse oximeter as recited in claim 4 wherein said signal combining means further comprises a digital to analog converter coupled to receive the modulation signal and constructed to convert the modulation signal to an analog signal.

10. The improved pulse oximeter as recited in claim 4 wherein said signal combining means further comprises a multiplexer for multiplexing the second control signal and the modulated control signal to said first light-emitting diode.

11. An improved pulse oximeter for measuring the oxygen saturation levels of a blood sample of a user, comprising:

a first light-emitting diode responsive to a first control signal and a modulated control signal for emitting light of a first predetermined frequency, said first light-emitting diode being constructed to be positioned proximate the user to emit light of the first predetermined frequency toward the user;

a second light-emitting diode responsive to a second control signal for emitting light of a second predetermined frequency, said second light-emitting diode being constructed to be positioned proximate the user to emit light of the second predetermined frequency toward the user;

a photodetector for detecting the light emitted by the first and second light-emitting diodes, said photodetector including an output and providing first, second, and third light detector output signals, the first light detector output signal being associated with light received from said first light-emitting diode in response to the first control signal, the second photodetector output being associated with light received from said second light-emitting diode in response to the second control signal, and the third light detector output signal being associated with light received from said first light-emitting diode in response to the modulated control signal;

first, second, and third analog to digital converters coupled to receive the first, second, and third photodetector output signals, respectively, said first, second, and third analog to digital converters being constructed to convert the first, second, and third photodetector output signals to respective first, second and third digital signals wherein the first digital signal is associated with light received from said first light-emitting diode in response to the first control signal, the second digital signal is associated with light received from said second light-emitting diode in response to the second control signal, and the third digital signal is associated with light received from said first light-emitting diode in response to the modulated control signal;

direct current signal processing means for removing the direct current component of the first, second, and third digital signals, said direct current signal processing means being further constructed to normalize the first digital signal with the direct current components of the first and second digital signals, said direct current signal processing means providing the normalized first digital signal with the direct current component removed as the first composite signal, the second digital signal with the direct current component removed as the second composite signal, and the third digital signal with the direct current component removed as the noise signal, wherein the first and second composite signals each include a desired signal portion and a noise signal portion;

first and second adaptive noise canceler means, said first adaptive noise canceler means being responsive to the first composite signal and the noise signal for removing the noise signal portion from the first composite signal to provide a first desired signal, said second adaptive noise canceler means being responsive to the second composite signal and the noise signal for removing the noise signal portion from the second composite signal to provide a second desired signal;

memory means for storing a lookup table for correlating values of a signal ratio to the percentage of oxygen in a user's blood;

data processing means for determining the signal ratio wherein the signal ratio is a ratio of the magnitudes of the first and second desired signals, said data processing means being further responsive to said memory means for determining the oxygen saturation level of the blood sample of the user, said data processing means being further constructed to combine the signal ratio and the second composite signal to provide a digital modulation signal, said data processing means also being constructed to sequentially provide the first control signal, the second control signal, and a third control signal;

a digital to analog converter coupled to receive the digital modulation signal and constructed to convert the digital modulation signal to an analog modulation signal and provide the analog modulation signal as its output;

a signal combiner for combining the analog modulation signal with the third control signal to provide the modulated control signal;

first, second, and third signal drivers for receiving the first, second and modulated control signals, respectively, and for supplying adequate power to the first, second, and modulated control signals to drive said first and second light-emitting diodes;

a multiplexer for multiplexing the first control signal and the modulated control signal to said first light-emitting diode; and display means responsive to said data processing means for displaying the percentage of oxygen in the user's blood sample.

12. An improved method for determining a signal ratio, wherein the signal ratio is combined with pulse oximetry lookup tables to determine the oxygen content of blood, the blood being positioned in a medium, said method comprising the steps of:

transmitting first and second light signals of respective first and second frequencies toward the medium;

transmitting a modulated light signal of the second frequency toward the medium, wherein the modulated light signal is a light signal of the second frequency modulated by a modulation signal;

detecting first and second composite signals respectively indicative of the amount of light transmitted through the medium by the first and second light signals, wherein the first and second composite signals each include a desired signal portion and a noise portion;

detecting a noise signal indicative of the amount of light transmitted though the blood by the modulated light signal;

combining the first composite signal with the noise signal to provide a first desired signal;

combining the second composite signal with the noise signal to provide a second desired signal;

determining the signal ratio as the ratio of the magnitudes of the first and second desired signals; and combining the signal ratio and the first composite signal to provide the modulation signal.

13. The method as recited in claim 12 wherein said step of combining the first composite signal with the noise signal to provide a first desired signal comprises the substep of adaptively processing the first composite signal with the noise signal to remove the noise portion from the composite signal.

* * * * *